(12) United States Patent
Faehsing

(10) Patent No.: US 10,973,562 B2
(45) Date of Patent: Apr. 13, 2021

(54) PLASMA SURGERY APPARATUS AND METHOD FOR OPERATING SUCH AN APPARATUS

(71) Applicant: OLYMPUS WINTER & IBE GMBH, Hamburg (DE)

(72) Inventor: Thomas Faehsing, Blankenburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 416 days.

(21) Appl. No.: 15/689,434

(22) Filed: Aug. 29, 2017

(65) Prior Publication Data

US 2017/0360496 A1    Dec. 21, 2017

Related U.S. Application Data

(63) Continuation of application No. PCT/EP2016/054641, filed on Mar. 4, 2016.

(30) Foreign Application Priority Data

Mar. 30, 2015  (DE) ............... 10 2015 205 729.1

(51) Int. Cl.
*A61B 18/04* (2006.01)
*A61B 18/12* (2006.01)
*A61B 18/00* (2006.01)

(52) U.S. Cl.
CPC ............ *A61B 18/042* (2013.01); *A61B 18/12* (2013.01); *A61B 2018/00589* (2013.01);
(Continued)

(58) Field of Classification Search
CPC .............. A61B 18/042; A61B 18/12; A61B 2018/00589; A61B 2018/00744;
(Continued)

(56) References Cited

U.S. PATENT DOCUMENTS 6,206,878 B1    3/2001  Bishop et al.
2008/0097425 A1*  4/2008  Truckai ................ A61B 18/042
                                                        606/41

(Continued)

FOREIGN PATENT DOCUMENTS

DE        600 23 876 T2     7/2006
DE     10 2014 003 382 A1   9/2014

*Primary Examiner* — Linda C Dvorak
*Assistant Examiner* — Annabeth E Rodriguez
(74) *Attorney, Agent, or Firm* — Oliff PLC

(57) ABSTRACT

A plasma surgery apparatus includes an HF generator for generating an HF activation signal, a gas source for providing a plasma gas, and a plasma applicator having a channel which opens out at a distal end of the applicator and through which the plasma gas can flow. The apparatus also includes an HF electrode that is electrically connected to the HF generator. When the HF electrode is supplied with the HF activation signal, a plasma is provided originating from the distal end of the applicator. The apparatus also includes a control unit and a flow regulator for regulating a flow rate the plasma gas in the channel. The control unit receives or requests an operating variable of the HF generator and, according to a saved functional relationship, controls the flow regulator so that the flow rate of the plasma gas is correlated with a detected value of the operating variable.

11 Claims, 1 Drawing Sheet

(52) U.S. Cl.
CPC ............ *A61B 2018/00648* (2013.01); *A61B 2018/00744* (2013.01); *A61B 2018/00827* (2013.01); *A61B 2018/00892* (2013.01)

(58) Field of Classification Search
CPC .... A61B 2018/00583; A61B 2018/122; A61B 2018/1472; A61B 2018/00636
See application file for complete search history.

(56) References Cited

U.S. PATENT DOCUMENTS

| | | | |
|---|---|---|---|
| 2011/0137308 A1* | 6/2011 | Woloszko | A61B 18/1485 606/41 |
| 2012/0022522 A1 | 1/2012 | Suslov | |
| 2014/0128714 A1* | 5/2014 | Banet | A61B 5/4848 600/391 |
| 2014/0257269 A1 | 9/2014 | Woloszko et al. | |
| 2014/0276725 A1* | 9/2014 | Cox | A61B 18/1402 606/33 |

* cited by examiner

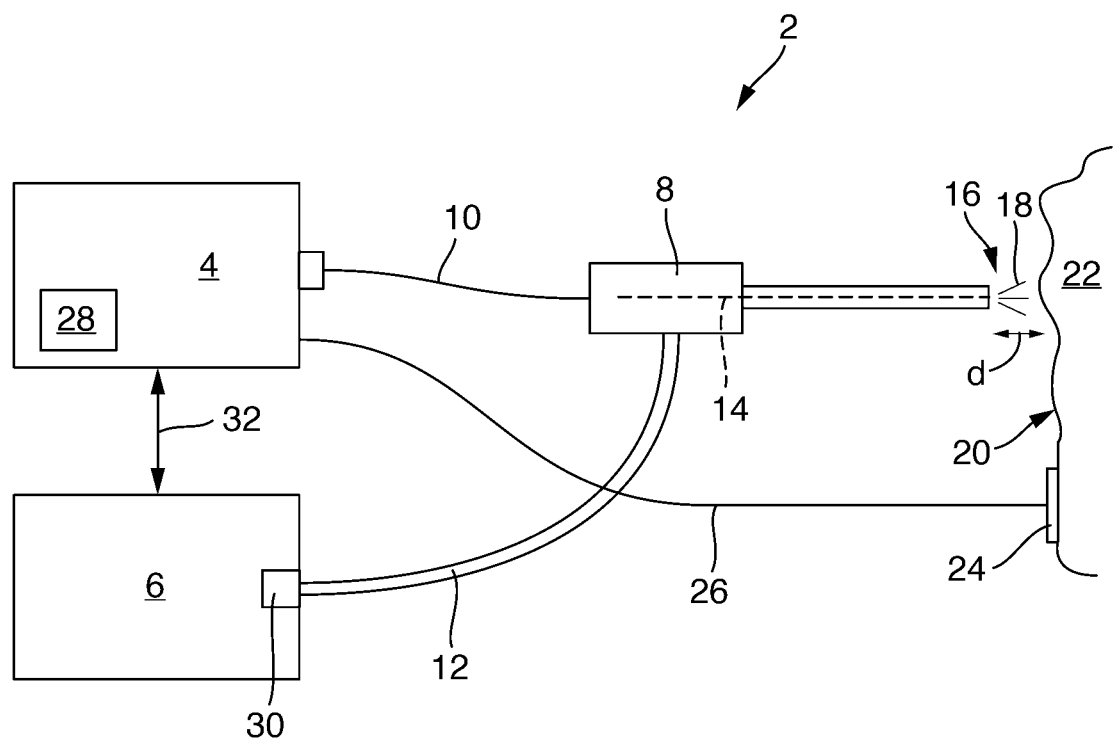

PLASMA SURGERY APPARATUS AND METHOD FOR OPERATING SUCH AN APPARATUS

CROSS REFERENCE TO RELATED APPLICATIONS

This application is a continuation of PCT/EP2016/054641 filed on Mar. 4, 2016, which in turn claims priority to DE 10 2015 205 729.1 filed on Mar. 30, 2015, the contents of which are incorporated by reference herein in their entirety.

BACKGROUND

The disclosed embodiments relate to a plasma surgery apparatus comprising a high frequency (HF) generator for generating an HF activation signal, a gas source for providing a plasma gas, and a plasma applicator having a channel which opens out at a distal end of the applicator and through which the plasma gas flows or can flow, and having an HF electrode that is preferably arranged in the channel and is electrically connected to the HF generator. The HF electrode is configured to be supplied with the HF activation signal to provide, originating from the distal end of the applicator, a plasma of the plasma gas that flows from the channel. The disclosed embodiments further relate to a method for operating such a plasma surgery system. Finally, the disclosed embodiments relate to a non-transitory computer readable medium.

Plasma surgery apparatuses such as argon plasma coagulation apparatuses are used in endoscopic medicine to stanch extensive bleeding. Another area of application for plasma surgery apparatuses is the extensive removal of tissue.

Plasma surgery apparatuses are based on the thermal effect of a high-frequency current which is applied to the tissue by an electrically ionizing plasma, in many cases an argon plasma. A plasma gas source and a high-frequency source are provided to generate the plasma. An HF electrode in an applicator is supplied with a high-frequency AC voltage so that the plasma forms between the tissue and a distal end of the applicator when the HF voltage is sufficiently high and the distance to the tissue is sufficiently small. The plasma formation is kept stable as plasma gas exits a distal end of the applicator.

The ionized plasma is electrically conductive so that an electrical current is applied into the tissue proceeding from the applicator. The current conducted through the plasma that contacts the tissue surface has a thermal effect that accordingly causes blood stanching, or respectively coagulation.

The penetration depth is limited so that deeper tissue layers are not affected. This spares the tissue and reduces the risk of perforation. Moreover, since the plasma does not propagate in a straight line but rather in a direction corresponding to the electrical field lines between the tissue and the applicator, areas that are difficult to access can be treated. Since coagulated tissue possesses a conductivity that is less than non-coagulated tissue, the electrical energy preferentially enters those areas where it is needed to stanch blood.

SUMMARY

An object of the disclosed embodiments is to present a plasma surgery apparatus, a method for operating a plasma surgery apparatus, and a non-transitory computer readable medium to improve plasma stability.

The object is achieved with a plasma surgery apparatus comprising an HF generator for generating an HF activation signal, a gas source for providing a plasma gas, and a plasma applicator having a channel which opens out at a distal end of the applicator and through which the plasma gas can flow, and having an HF electrode that is preferably arranged in the channel and is electrically connected to the HF generator. The HF electrode can be supplied with the HF activation signal such that, originating from the distal end of the applicator, a plasma of the plasma gas can be provided. The plasma surgery apparatus also comprises a control unit and a flow regulator for regulating a flow rate of plasma gas provided by the gas source in the channel. The control unit is configured to receive or request an operating variable of the HF generator and, according to a saved functional relationship, to control the flow regulator in such a way that the flow rate of the plasma gas is correlated with a detected value of the operating variable.

The plasma surgery apparatus is based on the following insights. At present, it is frequently routine to set the flow rate of the plasma gas before the start of treatment and leave it at a constant level during treatment. Apart from the distance of the instrument, or respectively the applicator, to the treated tissue, the plasma gas flow rate remains constant. It was recognized that when the plasma gas flow is constant, the coagulation result depends on the distance of the applicator to the tissue. In other words, the plasma and its quality depend on the plasma gas saturation between distal tip of the applicator and the tissue. When the distance between the distal tip of the applicator and the tissue is great, the plasma gas concentration close to the tissue may be too little for sufficiently stable plasma. The potential consequence is a plasma disruption followed by an automatic subsequent ignition attempt.

Based on these insights, it is proposed according to the disclosed embodiments to adapt the flow rate of the plasma gas to the distance of the applicator from the tissue. This includes both the initial adjustment of the flow rate as well as its dynamic regulation, or respectively control. It was moreover recognized that an operating variable of the HF generator can be evaluated as a measure or indication of the distance between the distal end of the applicator and the tissue. The flow rate of the plasma gas is modified depending on this parameter.

Accordingly, the flow rate is advantageously greater when the distance between the applicator and tissue is large than when the distance is small. This prevents a disruption of the plasma because a sufficiently large concentration of the plasma gas is always provided. At the same time, the consumption of plasma gas is optimized since only a small plasma gas flow is set when the distance is small. In contrast to conventional solutions that provide too much plasma gas in this operating mode, plasma gas is saved which yields cost advantages.

The plasma gas is for example argon.

The flow of the plasma gas is preferably automatically preset, or respectively regulated, on the basis of an effect selected by the user such as a coagulation effect. The extent of the selected effect, that for example is set or predetermined in any desired units, is converted or respectively translated into the electrical operating parameters of the HF generator. The plasma gas flow is then automatically set using the saved functional relationship based on the detected value of an operating variable of the HF generator. In particular, the user can influence the automatic presetting as desired, for example by adapting an offset or a slope of the saved functional relationship. To this end, the user is provided with a suitable operability, or respectively a suitable user interface.

Moreover, according to an advantageous development of the plasma surgery apparatus, it is further provided that the operating variable can change over time, and the control unit is configured to continuously change the flow rate over time corresponding to the saved functional relationship. In other words, the flow of the plasma gas is not just initially set depending on the operating variable of the HF generator; it is also readjusted depending on the time. This advantageously ensures that there is a sufficiently high plasma concentration at each point in time. Both an oversupply and undersupply of plasma gas are prevented.

In another advantageous embodiment, the flow rate of the plasma gas increases corresponding to the functional relationship as the value of the operating variable increases, and moreover the flow rate of the plasma gas decreases in particular as the value of the operating value falls. In particular, a proportional relationship is provided between the value of the operating variable and the flow rate.

Corresponding to the saved functional relationship, the flow of the plasma gas rises as the distance of the applicator increases, for example from a tissue wall. Of course, the value of the plasma gas flow rate decreases as the distance to the tissue wall shrinks. A proportional relationship between the value of the operating variable and the flow rate has proven to be particularly advantageous. Of course, other functional relationships are also provided that for example overproportionally reduce the plasma gas flow at low distances, and/or overproportionally increase it at large distances.

According to another advantageous embodiment, the operating variable is a DC offset voltage of the HF generator, an amplitude or an effective value of an HF current, and/or an HF voltage of the HF activation signal. In other words, the HF current and the HF voltage are an initial current, or respectively an initial voltage of the HF generator. When the plasma surgery apparatus is operating, an HF voltage is applied between the HF electrode and an electrode in contact with the tissue. An electric current flows in the plasma formed between the applicator and the tissue wall. This plasma discharge causes a DC offset in the applied HF activation signal, the value of which is stored in the HF generator. Likewise, the values of the amplitude or the effective value of the flowing HF current, and/or the applied HF voltage (of the HF activation signal) are stored in the HF generator.

It was moreover recognized that the values of the aforementioned electrical quantities such as the value of the DC offset voltage are a measure of the distance of the applicator from the tissue wall, for example. Accordingly, it is particularly effective and simple to regulate the flow rate of the plasma gas depending on one of the aforementioned quantities.

Stated more precisely, an initial stage of the HF generator is regulated while the plasma surgery apparatus is operating so that either a DC offset voltage, or the amplitude, or the effective value of the applied HF voltage, or the HF current is held at, or respectively close to a preset target value depending on the desired therapeutic effect. In addition, some or all of the other operating parameters are updated to achieve this regulation. It was moreover also recognized that each updated operating parameter can be a measure of the distance of the applicator from the tissue wall, for example. Accordingly, it is particularly effective and simple to regulate the flow rate of the plasma gas depending on the respective updated operating parameter.

According to another advantageous embodiment, it is provided that the plasma surgery apparatus is a plasma coagulation apparatus.

The object is further achieved by a method for operating a plasma surgery apparatus according to one or more of the aforementioned embodiments. In such a method, an HF activation signal is generated by the HF generator, and the plasma gas is provided from the gas source. The plasma gas flows through the applicator channel and the HF activation signal is applied to the electrode so that the plasma is provided at the distal end of the applicator. The control unit receives or requests the operating variable of the HF generator and controls the flow regulator corresponding to the saved functional relationship so that the flow rate of the plasma gas is correlated to the detected value of the operating variable.

The same or similar advantages as already mentioned with regard to the plasma surgery apparatus also relate to the method for operating said apparatus and will therefore not be repeated.

According to an advantageous embodiment, the method is developed in that the operating variable changes with time, and the control unit is configured to continuously change the flow rate over time corresponding to the saved functional relationship.

According to another advantageous embodiment, the flow rate of the plasma gas increases as the value of the operating variable rises, wherein in particular the flow rate of the plasma gas is proportionally changed depending on the value of the operating variable.

Finally, the method for operating a plasma surgery apparatus is advantageously developed in that a DC offset voltage of the HF generator, an amplitude or an effective value of an HF current and/or an HF voltage of the HF activation signal is received or requested as the operating variable.

The object according to the invention is furthermore achieved by a non-transitory computer readable medium storing a program that causes a plasma surgery apparatus according to one or more of the cited embodiments to execute a method according to one or more of the cited embodiments. The same or similar advantages as already explained with respect to the plasma surgery apparatus also apply to the non-transitory computer readable medium.

Further features of the invention will become apparent from the description of embodiments according to the invention together with the claims and the included drawing. Embodiments according to the invention can fulfill individual characteristics or a combination of several characteristics.

BRIEF DESCRIPTION OF THE DRAWING

The FIGURE shows a pharmaceutical apparatus of the disclosed embodiments in a schematically simplified perspective representation.

DETAILED DESCRIPTION OF EMBODIMENTS

The FIGURE illustrates a pharmaceutical apparatus 2 of the disclosed embodiments in a schematically simplified representation. It comprises an HF generator 4 for generating an HF activation signal. Moreover, there is a gas source 6 that provides a plasma gas such as argon. A plasma applicator 8 is connected both to the HF generator 4 via a suitable HF connecting cable 10, as well as to the gas source 6 via a suitable gas connecting hose 12.

Within the interior of the applicator 8, there is a channel 14—schematically indicated with a dashed line—that terminates at a distal end 16 of the applicator 8. The plasma gas that is supplied by the gas source 6 to the plasma applicator 8 flows through the channel 14 while the plasma surgery apparatus 2 is operating. An HF electrode (not shown) that is electrically connected to the HF generator 4 is arranged in the channel 14 of the plasma applicator 8. An HF activation signal is applied to this HF electrode and is transmitted via the HF connecting cable 10 by the HF generator 4 to the plasma applicator 8.

The plasma gas in the channel 14 is ionized so that a plasma 18 is provided at the distal end 16 of the applicator 8. The plasma 18 is applied to a surface 20 of the tissue 22. The tissue 22 is for example human or animal tissue of an organ, wherein the surface 22 is correspondingly an organ wall, for example.

Proceeding from the plasma applicator 8, electrical energy is transmitted via the ionized and hence electrically conductive plasma 18 to the surface 20 of the tissue 22. There, the electrical energy produces local heating of the tissue 22 which for example causes coagulation, i.e., blood stanching, on the surface 20. In other words, the described plasma surgery apparatus 2 is preferably a plasma coagulation apparatus, in particular an argon plasma coagulation apparatus.

Due to the low penetration depth of the thermal energy transmitted by the plasma 18, deeper tissue layers are not affected and are spared so that there is only a slight perforation risk for the surface 20 due to the slight penetration depth. The electrical conductivity of already coagulated tissue is furthermore less than that of uncoagulated tissue; consequently, energy is preferentially supplied where local bleeding still needs to be stanched.

The plasma surgery apparatus 2 furthermore comprises a neutral electrode 24 that, to the extent it is a monopolar apparatus, is extensively in contact with the patient to be treated. It is further provided that the neutral electrode 24 is placed directly in or on the tissue 22 (as indicated in the FIGURE) where the bleeding needs to be stanched. The neutral electrode 24 is coupled to the HF generator 4 by a corresponding return line 26.

The plasma surgery apparatus 2 furthermore comprises a control unit 28 that is only represented for example as part of the HF generator 4. There is also a flow regulator 30.

The flow regulator 30 regulates a flow rate of the plasma gas provided by the gas source 6 in the channel 14 of the plasma applicator 8. The control unit 28 is configured to receive or request an operating variable of the HF generator 4. This operating variable is for example a DC offset voltage of the HF generator 4.

The control unit 28 is furthermore configured to control the flow regulator 30 corresponding to the saved functional relationship so that the flow rate of plasma gas in the channel 14 correlates to the detected value of the operating variable of the HF generator 4. For this purpose, the HF generator 4 and the gas source 6 are coupled with each other by a suitable data link 32.

According to another exemplary embodiment, the control unit 28 is configured to not only control the flow rate of the plasma gas in the channel 14, but also to regulate the flow rate with feedback. For this purpose, a flow controller (not shown) is provided in the channel 14.

The plasma surgery apparatus 2 is preferably configured so that the operating variable, such as the DC offset voltage of the HF generator 4, can change over time, and is detected, or respectively requested by the control unit 28 as a quantity that changes over time. The control unit 28 is correspondingly configured to change, or to respectively readjust or adapt the flow rate of the plasma gas in the channel 14 continuously over time corresponding to the saved functional relationship.

In other words, the control unit 28 adjusts the required flow rate of the plasma gas in the channel 14 initially when the plasma surgery apparatus 2 starts up, and also dynamically updates the flow rate during operation. This advantageously makes it possible to adapt the flow of the plasma gas in the channel 14 when the distance d changes between the distal end 16 of the plasma applicator 8 and the surface 20 of the tissue 22.

Whereas a slight flow of the plasma gas is sufficient at a slight distance d to maintain the plasma 18, an increasing amount of plasma gas is needed as the distance d increases to prevent the plasma 18 from being disrupted. This advantageously ensures that the plasma 18 is reliably maintained even when the distance d between the surface 20 of the tissue 22 and the distal end of 16 of the plasma applicator 8 changes. At the same time, the amount of the plasma gas used is optimized so that an unnecessary amount of plasma gas is not used. This improves the efficiency of the plasma surgery apparatus 2.

The functional relationship saved in the control unit 28 controls the above-described functionality between the plasma gas flow in the channel 14 of the plasma applicator 8 and the distance d. For this purpose, the control unit 28 continuously queries for example a DC offset voltage of the HF generator 4 and controls the flow regulator 30 of the gas source 6 via the data link 32 corresponding to the saved functional relationship between the operating variable of the HF generator 4 (DC offset voltage) and the flow rate of the plasma gas. A proportional relationship between the value of the operating variable and the flow rate has proven to be particularly advantageous.

According to one method for operating the plasma surgery apparatus 2 according to one or more of the aforementioned features according to the disclosed embodiments, an HF activation signal is generated by the HF generator 4, and the plasma gas is provided by the gas source 6. Plasma gas flows through the channel 14 of the plasma applicator 8, and the HF activation signal is applied to the electrode (not shown). The plasma 18 is provided at the distal end of 16 of the applicator 8. The control unit 28, which receives or queries the operating variable of the HF generator 4, controls the flow regulator 30 corresponding to the saved functional relationship so that the flow rate of the plasma gas in the channel 14 correlates with the detected value of the operating variable.

This control is in particular continuous over time corresponding to the functional relationship saved in the control unit 28. Furthermore, it is preferably provided that the flow of the plasma gas is also increased as the value of the operating variable increases, for example as the DC offset voltage increases, which indicates an increasing distance d between the distal end 16 of the plasma applicator 8 and the surface 20 of the tissue 22. The same also applies conversely; accordingly, the flow of the plasma gas is reduced as the distance d decreases.

The control unit 28 is preferably an arithmetic unit that has the generally known components. For example, the control unit 28 that is for example a computer, workstation or microcontroller, comprises a non-volatile memory in which inter alia the functional relationship is saved.

Furthermore, the control unit 28 is configured to run a computer program stored on a non-transitory computer readable medium, which causes the plasma surgery apparatus 2 to perform the above-explained method. The computer program is also saved in the non-volatile memory of the control unit 28.

What is claimed is:

1. A plasma surgery apparatus for operating on a tissue, the apparatus comprising:
    an HF generator configured to generate a high frequency (HF) activation signal;
    a gas source configured to provide a plasma gas;
    a plasma applicator having a channel which opens out at a distal end of the applicator and through which the plasma gas can flow;
    an HF electrode that is electrically connected to the HF generator, wherein the HF electrode is configured to be supplied with the HF activation signal to provide, originating from the distal end of the applicator, a plasma of the plasma gas that flows from the channel;
    a flow regulator configured to regulate a flow rate of the plasma gas provided by the gas source in the channel; and
    a control unit configured to receive or request an operating variable of the HF generator and, according to a saved functional relationship, to control the flow regulator such that the flow rate of the plasma gas is correlated with a detected value of the operating variable,
    wherein the operating variable is a DC offset voltage of the HF generator, the DC offset voltage being a measure of a distance of the plasma applicator from the tissue.

2. The apparatus according to claim 1, wherein the operating variable can change over time, and the control unit is configured to continuously change the flow rate over time corresponding to the saved functional relationship.

3. The apparatus according to claim 1, wherein the flow regulator is configured to regulate the flow rate of the plasma gas so that the flow rate increases corresponding to the functional relationship as the value of the operating variable increases.

4. The apparatus according to claim 3, wherein, the value of the operating variable and the flow rate have a proportional relationship.

5. The apparatus according to claim 1, wherein the plasma surgery apparatus is a plasma coagulation apparatus.

6. The apparatus according to claim 1, wherein the HF electrode is arranged in the channel.

7. A method for operating the plasma surgery apparatus according to claim 1, comprising:
    providing the plasma gas from the gas source so that the plasma gas flows through the channel of the plasma applicator; and
    generating the HF activation signal by the HF generator and transmitting the HF activation signal to the electrode so that the plasma is provided at the distal end of the applicator,
    wherein the control unit receives or queries the operating variable of the HF generator and controls the flow regulator corresponding to the saved functional relationship so that the flow rate of the plasma gas is correlated to the detected value of the operating variable.

8. The method according to claim 7, wherein the operating variable can change over time, and the control unit is configured to continuously change the flow rate over time corresponding to the saved functional relationship.

9. The method according to claim 7, wherein the flow rate of the plasma gas increases as the value of the operating variable rises.

10. The method according to claim 9, wherein the flow rate of the plasma gas is proportionally changed depending on the value of the operating variable.

11. A non-transitory computer readable medium storing a program that causes the plasma surgery apparatus according to claim 1 to perform the following functions:
    providing the plasma gas from the gas source so that the plasma gas flows through the channel of the plasma applicator; and
    generating the HF activation signal by the HF generator and transmitting the HF activation signal to the electrode so that the plasma is provided at the distal end of the applicator,
    wherein the control unit receives or queries the operating variable of the HF generator and controls the flow regulator corresponding to the saved functional relationship so that the flow rate of the plasma gas is correlated to the detected value of the operating variable.

* * * * *